US009529503B2

(12) United States Patent
Guthrie et al.

(10) Patent No.: US 9,529,503 B2
(45) Date of Patent: Dec. 27, 2016

(54) ANALYTE-MEASUREMENT SYSTEM RECORDING USER MENU CHOICES

(71) Applicant: LifeScan Scotland Limited, Inverness-shire (GB)

(72) Inventors: Brian Guthrie, Inverness-shire (GB); Malcolm D Hamer, Highlands (GB); Alexander Strachan, Moray (GB); Kimberley A. Gibson, Inverness (GB); Jonathan Nelson, Inverness-shire (GB)

(73) Assignee: LifeScan Scotland Limited, Inverness (GB)

( * ) Notice: Subject to any disclaimer, the term of this patent is extended or adjusted under 35 U.S.C. 154(b) by 152 days.

(21) Appl. No.: 13/928,785

(22) Filed: Jun. 27, 2013

(65) Prior Publication Data
US 2015/0007107 A1    Jan. 1, 2015

(51) Int. Cl.
G06F 3/0484    (2013.01)
G06F 19/00    (2011.01)

(52) U.S. Cl.
CPC ......... *G06F 3/0484* (2013.01); *G06F 19/3406* (2013.01)

(58) Field of Classification Search
CPC ... G06F 19/3406; G06F 19/36; G06F 19/3412
USPC ....................................... 715/810
See application file for complete search history.

(56) References Cited

U.S. PATENT DOCUMENTS

| 4,680,729 A | * | 7/1987 | Steinhart | G06F 3/0238 341/29 |
| 6,151,586 A | | 11/2000 | Brown | |
| 6,179,979 B1 | | 1/2001 | Hodges et al. | |
| 6,444,115 B1 | | 9/2002 | Hodges et al. | |
| 7,276,029 B2 | | 10/2007 | Goode, Jr. et al. | |
| 7,912,655 B2 | | 3/2011 | Power et al. | |
| RE43,316 E | * | 4/2012 | Brown et al. | 600/309 |
| 8,163,162 B2 | | 4/2012 | Chatelier et al. | |

(Continued)

FOREIGN PATENT DOCUMENTS

| EP | 2455877 A2 | 5/2012 |
| EP | 2590098 A1 | 5/2013 |
| WO | 2011106030 A1 | 9/2011 |

OTHER PUBLICATIONS

International Search Report and Written Opinion issued in related International Patent Application No. PCT/EP2014/063601, dated Nov. 11, 2014, 15 pages.

(Continued)

*Primary Examiner* — Ryan Barrett
*Assistant Examiner* — David Luu

(57) ABSTRACT

An analyte measurement system includes a processor connected to a biosensor providing analyte data corresponding to an analyte level of a fluid sample. A user interface provides a menu of functions to a user and successively receives a plurality of menu choices, which the processor records. A storage device holds data defining a first action criterion. The processor compares the menu choices to the first action criterion. When the stored menu choices satisfy the first action criterion, the processor can automatically add a first additional function to the menu of functions, or can automatically presents a reward token via the user interface. The system can also include a housing holding the user interface, the storage device, and the processor. Methods are also disclosed.

10 Claims, 6 Drawing Sheets

(56) References Cited

U.S. PATENT DOCUMENTS

| | | |
|---|---|---|
| 8,719,056 B1* | 5/2014 | Bartley et al. .................... 705/3 |
| 2004/0141011 A1* | 7/2004 | Smethers .............. G06F 3/0482 |
| | | 715/810 |
| 2008/0015422 A1* | 1/2008 | Wessel .......................... 600/301 |
| 2008/0255438 A1 | 10/2008 | Saidara et al. |
| 2009/0058816 A1* | 3/2009 | Takeuchi ...................... 345/169 |
| 2010/0138794 A1* | 6/2010 | Ganey ................. G06F 3/04817 |
| | | 715/853 |
| 2010/0261987 A1* | 10/2010 | Kamath et al. ............... 600/365 |
| 2011/0137571 A1 | 6/2011 | Power et al. |
| 2011/0193704 A1* | 8/2011 | Harper et al. ............. 340/573.1 |
| 2011/0237227 A1* | 9/2011 | Kemery ............. G06F 21/6218 |
| | | 455/414.1 |
| 2011/0287528 A1* | 11/2011 | Fern et al. ................. 435/287.1 |
| 2012/0232520 A1 | 9/2012 | Sloan et al. |
| 2012/0271655 A1 | 10/2012 | Knobel et al. |
| 2013/0172688 A1* | 7/2013 | Allen et al. ................... 600/301 |
| 2014/0303466 A1* | 10/2014 | Fitzpatrick et al. .......... 600/365 |

OTHER PUBLICATIONS

Clark, P., "Nectar . . . details of the UK coalition loyalty programme," The Wise Marketer, Sep. 2002, retrieved Jun. 1, 2013 from http://www.thewisemarketer.com/features,read.asp?id=15, 14.

\* cited by examiner

ANALYTE-MEASUREMENT SYSTEM RECORDING USER MENU CHOICES

TECHNICAL FIELD

This application relates generally to the field of analyte measurement systems and more specifically to analyte measurement systems that receive menu choices via a user interface.

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and hypoinsulinemia have been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose (BG) within normal limits. Such glycemic control is achieved by regularly supplying external insulin to the body of the patient to thereby reduce the elevated levels of blood glucose.

External biologic agents such as insulin can be administered as multiple daily injections of a mixture of rapid and intermediate-acting drugs via a hypodermic syringe. Improved glycemic control can be achieved by the so-called "intensive hormone" therapy which is based on multiple daily injections, including one or two injections per day of a long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections. For some patients, substantial improvements in diabetes therapy have been achieved by the development of drug delivery devices, such as pumps, that relieve the patient of the need for syringes or drug pens and the need to administer multiple daily injections. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch.

Blood or interstitial analyte monitoring can be used to achieve acceptable glycemic control. The determination of blood glucose concentration can be performed by means of an episodic measuring device, such as a hand-held electronic meter that receives blood samples on enzyme-based test strips and calculates the blood glucose value based on an electrochemical reaction of the blood and the enzyme. Continuous glucose monitoring (CGM) using a sensor inserted into or implanted in the body can also be used.

Many patients use episodic measuring of blood glucose. This approach is straightforward but requires regular attention from the patient. Even patients using CGM and insulin pumps are generally required to check their blood-glucose readings throughout the day and consume sugars as necessary to forestall hypoglycemia. The required level of attention can be discouraging for some patients. Moreover, as glucose-monitoring and glucose-control systems become more complex, it can be difficult for some patients to effectively use their glucose meters or drug-delivery devices.

Besides glucose, there are other analytes of interest such as, for example, ketone or cholesterol, which can be monitored by a person with diabetes or other chronic diseases. It is believed that these analyte meters suffer from the same shortcomings as the glucose meter.

SUMMARY OF THE DISCLOSURE

In one embodiment, therefore, we have devised an analyte measurement system. The system may include the following components:
 a) a biosensor adapted to receive a fluid sample and provide analyte data corresponding to an analyte level of the fluid sample;
 b) a user interface adapted to provide a menu of functions to a user and successively receive a plurality of menu choices;
 c) a storage device holding data defining a first action criterion; and
 d) a processor operatively connected to the user interface, the biosensor, and the storage device and configured to record the received menu choices and compare the menu choices to the first action criterion, so that when the stored menu choices satisfy the first action criterion, the processor automatically adds a first additional function to the menu of functions.

In another embodiment, we have devised an analyte measurement apparatus. The apparatus may include the following components:
 a) a biosensor adapted to receive a fluid sample and provide analyte data corresponding to an analyte level of the fluid sample;
 b) a user interface adapted to provide a menu of functions to a user and successively receive a plurality of menu choices;
 c) a storage device holding data defining a first action criterion;
 d) a processor operatively connected to the user interface, the biosensor, and the storage device and configured to record the received menu choices and compare the menu choices to the first action criterion, so that when the stored menu choices satisfy the first action criterion, the processor automatically presents a reward token via the user interface; and
 e) a housing holding the user interface, the storage device, and the processor.

These embodiments exemplary of the present invention provide improved value to users of blood-analyte (e.g., glucose, ketone, cholesterol and the likes) measurement devices. Various embodiments customize the user interface of a device to its particular user by adding functions corresponding to the ways the user is using the device. Various embodiments provide users incentives to use their devices, and permit healthcare providers to customize those incentives.

Accordingly, in any of the embodiments described earlier, the following features may also be utilized in various combinations with the previously disclosed embodiments. For example, the analyte measurement system can include the storage device holding the data further defining a second action criterion, the data that define the second action criterion including a requirement that the first action criterion be satisfied, the processor further configured to compare the menu choices to the second action criterion, so that when the stored menu choices satisfy the second action criterion, the processor automatically adds a second additional function to the menu of functions; the processor further configured to successively record a plurality of values of the analyte data and to analyze the recorded analyte values, the data that define the first action criterion including a requirement that the recorded analyte values be within a selected range during a selected time period; the storage device holding the data that define the first action criterion further including a requirement that the recorded analyte values be within a second selected range during a second selected time period, the second selected range being a proper subset of the selected range and the second selected time period following after the selected time period; the storage device holding the data that define the first action criterion including a requirement that a selected one of the menu choices be received at least a selected number of times during a selected time period; the user interface including an external connection terminal, one of the functions in the menu being establishing a data connection via the external connection terminal, and the data that define the first action criterion including a requirement that the data connection be established; the external connection terminal including a mechanical cable connector, the user interface further including a wireless external connection terminal, and the first function being wireless communications via the wireless external connection terminal; the storage device holding data defining the first function, the first function being selected from the group consisting of meal tagging, pattern messaging, wireless communication, storage and display of a plurality of values of the analyte data, and time averaging over a selected time period shorter than 30 days; the storage device holding the data that define the first criterion including a requirement selected from the group consisting essentially of transmitting one or more values of the analyte data via an external connection terminal of the analyte measurement system, more than a selected number of times per day, receiving a menu choice to test blood analyte using the biosensor, more frequently than a selected frequency, receiving a menu choice to test blood analyte using the biosensor, and combinations thereof; or the processor further configured to, after adding the first additional function to the menu of functions, present a notification corresponding to the first additional function via the user interface.

In other examples, the analyte measurement apparatus can include the processor configured to present a unique redemption code as the reward token, the redemption code comprising one or more letters, numbers, accents, punctuation marks, ideographic or syllabic signs, whitespace characters, or combinations thereof; the storage device further holding a unique identifier, the processor configured to determine the unique redemption code using the stored unique identifier; the user interface including a soft-copy display or an audio output, the processor configured to present the unique redemption code by displaying a visual representation of the unique redemption code on the soft-copy display or by playing an audio representation of the unique redemption code via the audio output; the storage device further holding instructional data corresponding to the first reward token and the processor further configured to present the stored instructional data with the reward token via the user interface; the instructional data including an explanatory message selected from the group consisting of a message indicative that the code is redeemable for a replacement battery, a message indicative that the code is redeemable for a pharmaceutical or first-aid item, a message indicative that the code is redeemable for a discount at a retailer, and a message indicative that the code is redeemable for graphical or auditory content to be presented via the user interface; the storage device holding a plurality of point increments corresponding to a plurality of the functions, the processor being further configured to add to a stored point total the stored point increment for each of the received menu choices, and the data that define the first action criterion including a requirement that the stored point value reach a selected point threshold; the processor further configured to present the reward token by providing a unique redemption code and deducting the selected point threshold from the stored point total; the storage device storing a target blood-analyte range, a target time period, and a corresponding target point increment, the processor further configured to successively record a plurality of values of the analyte data and to analyze the stored values, so that the processor adds the target point increment to the stored point total when the stored values are within the target range during the target time period; the processor further configured to determine a future portion of the target time period and provide an indication to the user of the determined future portion and the target point increment; the processor further configured to use the stored menu choices to determine a function that does not correspond to a menu choice received within a selected time period, so that the processor provides an indication via the user interface of the determined function and the corresponding stored point increment; or the storage device holding data defining the functions including one or more selected from the group consisting essentially of a blood analyte test performed with the biosensor, a control-solution test performed with the biosensor, a unique identifier of a package of biosensors entered in the processor, one or more values of the analyte data transmitted via an external connection terminal of the analyte measurement system, and combinations thereof.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the terms "about" or "approximately" for any numerical values or ranges indicate a suitable dimensional tolerance that allows the part or collection of components to function for its intended purpose as described herein. Throughout this disclosure, the terms "patient" and "subject" are used interchangeably. These terms can refer to any human or animal subject and are not intended to limit the systems or methods to human use, although use of the subject invention in a human patient represents a preferred embodiment. Furthermore, in this disclosure, the term "user" can refer to a patient using a analyte measuring device or another person (e.g., a parent or guardian, nursing staff member, home care employee, or other caretaker) using a analyte measuring device. The term "drug" may include hormones, biologically active materials, pharmaceuticals or other chemicals that cause a biological response (e.g., a glycemic response) in the body of a user or patient. Throughout this disclosure, exemplary blood glucose levels are given in mg/dL. These levels can be divided by 18 to obtain mmol/L. Intervals or other numerical ranges are denoted using parentheses for open endpoints (the value of the endpoint is not included in the interval) and square brackets for closed endpoints (the value of the endpoint is included in the interval), as is common in the mathematical art.

Figure 1:
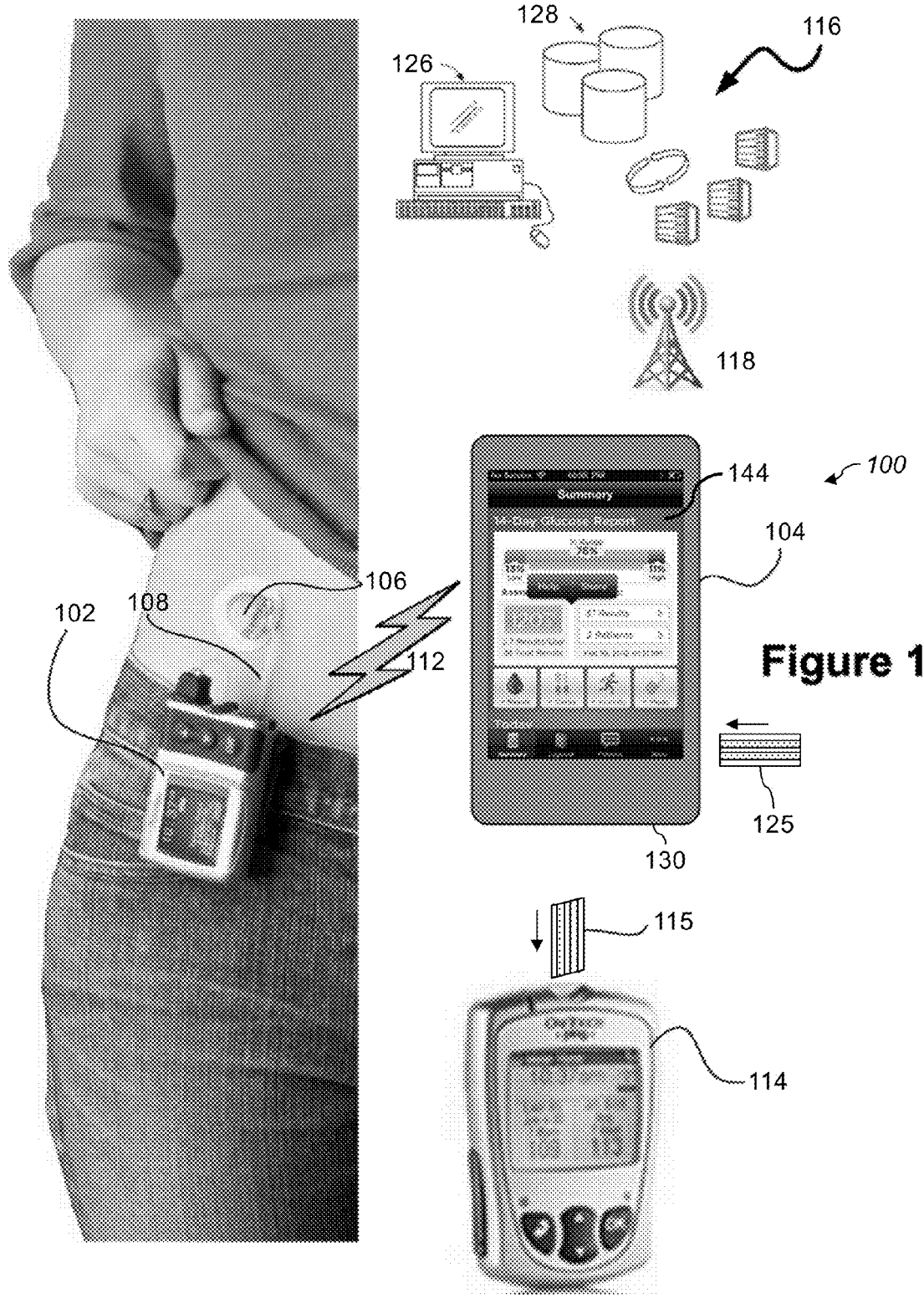
FIG. 1 illustrates an exemplary analyte-monitoring and drug-delivery system.

FIG. 1 illustrates an analyte-monitoring and drug-delivery system 100 according to an exemplary embodiment. The system 100 includes a drug delivery device 102 and a controller 104. The drug delivery device 102 is connected to an infusion set 106 via flexible tubing 108. Various embodiments of the invention can also be used with injections via syringe or insulin pen instead of or in addition to infusion via the drug delivery device 102. Various embodiments of the invention can also be used with injections via syringe or insulin pen instead of or in addition to infusion via the drug delivery device 102. In various examples, the controller 104 for the drug delivery device 102 (e.g., an infusion pump) or a analyte meter 114 is separate from both the drug delivery device 102 and the analyte meter 114, and the controller 104 can be connected to a network to provide near real-time monitoring.

The drug delivery device 102 is configured to transmit and receive data to and from the controller 104 by, for example, a radio frequency (RF) communication link 112. The drug delivery device 102 may also function as a stand-alone device with its own built in controller. In one embodiment, the drug delivery device 102 is an insulin infusion device and the controller 104 is a hand-held portable controller. In such an embodiment, data transmitted from the drug delivery device 102 to the controller 104 may include information such as, for example, insulin delivery data, blood analyte information, basal, bolus, insulin to carbohydrates ratio or insulin sensitivity factor. Data transmitted from the controller 104 to the drug delivery device 102 may include glucose test results and a food database to allow the drug delivery device 102 to calculate the amount of insulin to be delivered by the drug delivery device 102. Alternatively, the controller 104 may perform basal dosing or bolus calculation and send the results of such calculations to the drug delivery device.

Analyte levels or concentrations in physiological fluid (e.g., blood, saliva, or interstitial fluid) of a subject can be determined by the use of the analyte meter 114. The analyte meter 114 utilizes amperometric electrochemical sensor technology to measure analyte. The analyte meter 114 (here, an episodic meter) provides data to either or both of the controller 104 and the drug delivery device 102. The analyte meter 114 can measure a fluid sample placed on a test strip 115. The two hatched areas on the test strip 115 represent two electrodes, as is discussed below with reference to FIG. 2. The controller 104 can present information and receive commands via a touchscreen 144 or other devices, discussed below with reference to the user interface 330, FIG. 3.

In various embodiments, the controller 104 is combined with the analyte meter 114 into an integrated monolithic device having a housing 130. This integration is represented by an exemplary test strip 125. In other embodiments, the controller 104 and the analyte meter 114 are two separable devices that are dockable with each other to form an integrated device. Each of the devices 102, 104, and 114 has a suitable micro-controller (not shown for brevity) programmed to carry out various functionalities. Examples of micro-controllers that can be used are discussed below with reference to a processor 386, FIG. 3.

The drug delivery device 102 or the controller 104 can be configured for bi-directional communication with a network 116 through, for example, a wireless communication network 118, or a wired communications network such as a telephone or Ethernet connection. The network 116 can be the Internet or another TCP/IP, IPX/SPX, or X.25 network. One or more server(s) 126 or storage device(s) 128 can be communicatively connected to the controller 104 via the network 116.

The drug delivery device 102 can include electronic signal processing components including a central processing unit and memory elements for storing control programs and operation data, a radio frequency module (not shown) for sending and receiving communication signals (e.g., messages) to/from the controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a insulin from a insulin reservoir (e.g., a insulin cartridge) through a side port connected via the flexible tubing 108 to an infusion set 106 and into the body of the user.

Various analyte management systems include an episodic glucose sensor (e.g., a glucose meter 114) and an infusion pump. An example of such a system is OneTouch Ping® Glucose Management System manufactured and sold by the Animas Corporation. The "ezBG" feature of this system computes an amount of insulin to be delivered by the infusion pump using the results of an episodic glucose measurement.

Figure 2:
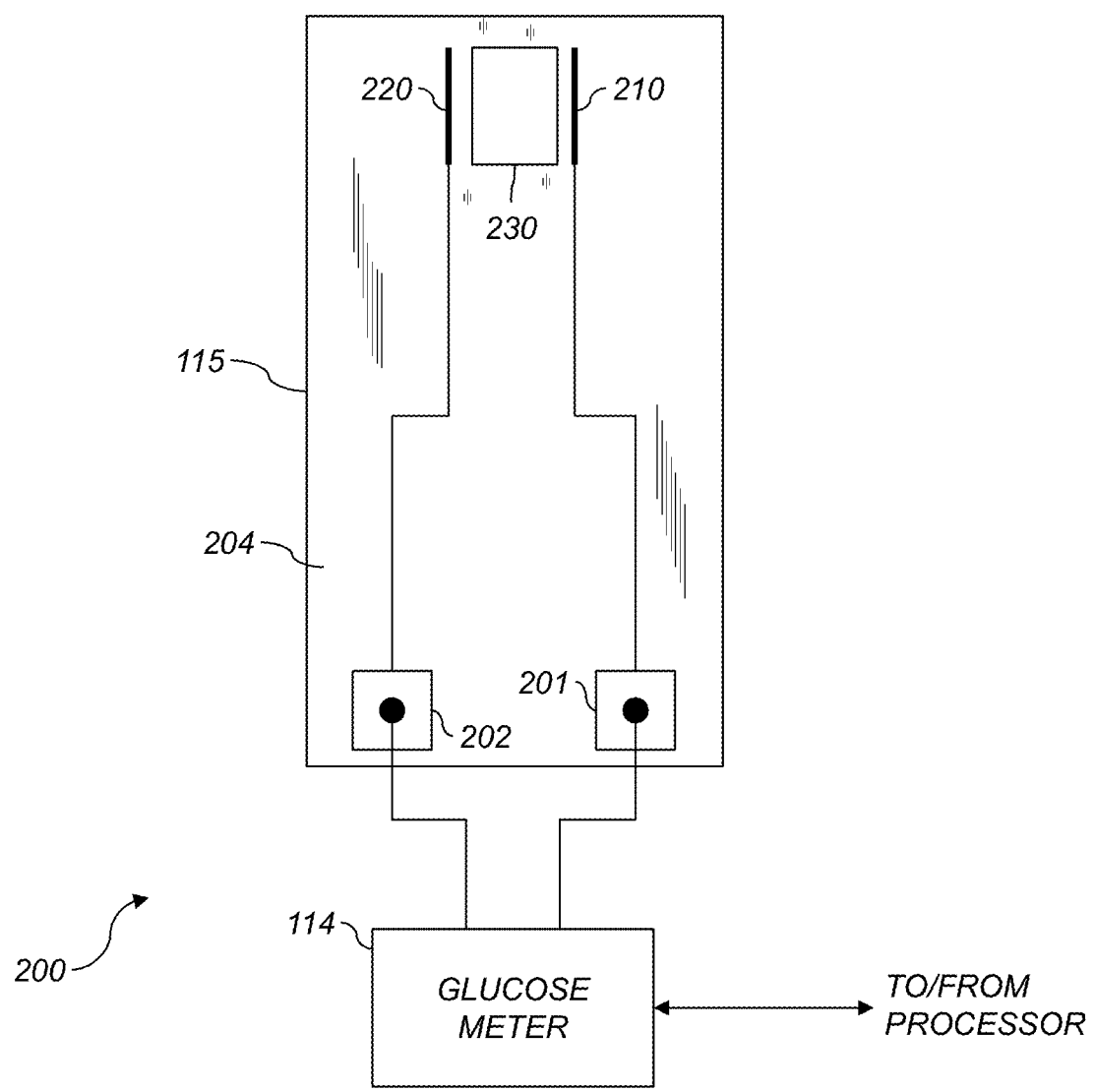
FIG. 2 shows an exemplary biosensor.

FIG. 2 shows an exemplary biosensor 200 for use in an episodic analyte meter. The biosensor 200 is defined by a test strip 115 electrically connected to the analyte meter 114. The test strip 115 is defined by a planar substrate 204 over which are disposed electrodes 210, 220 and electrical contact pads 201, 202. The electrodes 210, 220 can be disposed on opposing sides of a sample-receiving chamber 230, above and below the sample-receiving chamber 230, or in other configurations. The analyte meter 114 can communicate with a processor, e.g., the controller 104, FIG. 1.

In the exemplary test strip 115, the electrode 220 is a working electrode formed by sputtering a Pd coating on a polyester base forming the planar substrate 204. A dry reagent layer is used and includes buffer, mediator, and enzyme, as described herein. The electrode 210 is a reference electrode formed by sputtering an Au coating on the polyester base forming the planar substrate 204. The electrical contact pads 201, 202 connect to the electrodes 210, 220, respectively, and permit applying or detecting electrical signals across the sample-receiving chamber 230 between the electrodes 210, 220. The sample-receiving chamber 230 can have a volume ranging from, e.g., about 0.1 microliters to about 5 microliters. Various enzymes in the sample-receiving chamber 230 can assist in transducing the analyte (e.g., glucose) in the fluid sample (e.g., blood) into a current, potential, or other quantity that can be measured electrically. Exemplary enzymes include glucose oxidase, glucose dehydrogenase (GDH) based on a pyrroloquinoline quinone co-factor, and GDH based on a nicotinamide adenine dinucleotide co-factor.

In use, top ends of the electrodes 210, 220 are in contact with an electrolyte phase (not shown), which is a free-flowing fluid phase (e.g., a blood sample) disposed between the electrodes 210, 220. An enzyme, e.g., glucose oxidase, can cover the electrolyte phase. Depending on the state of the test strip 200, the electrode 210 can be a working electrode and the electrode 220 can be a counter electrode. In an example using glucose oxidase, a current is produced at the working electrode (and flows through the circuitry to the counter electrode). That current is representative of the concentration of analyte in the subject's body. The analyte meter 114 can measure the current through the electrodes 210, 220 to determine the analyte level of the fluid sample in the sample-receiving chamber 230. Exemplary glucose sensors and associated components are shown and described in U.S. Pat. Nos. 6,179,979, 8,163,162, and 6,444,115, which are incorporated by reference herein in their entireties.

Continuous glucose monitors (CGMs) can also be used as biosensors, e.g., as described in U.S. Pat. No. 7,276,029, incorporated by reference herein. An exemplary CGM sensor uses amperometric electrochemical sensor technology to measure an analyte. The CGM sensor includes three electrodes operably connected to the sensor electronics and covered by a sensing membrane and a biointerface membrane, which are attached by a clip. The top ends of the electrodes are in contact with an electrolyte phase, which is a free-flowing fluid phase disposed between the sensing membrane and the electrodes. The sensing membrane may include an enzyme, e.g., analyte oxidase, which covers the electrolyte phase. The $H_2O_2$ produced from the analyte oxidase reaction further reacts at the surface of working electrode and produces two protons (2H+), two electrons (2e−), and one oxygen molecule ($O_2$). A potentiostat is used to measure the electrochemical reaction(s) at the electrode(s) by applying a constant potential between the working and reference electrodes to produce a current value. The current that is produced at the working electrode (and flows through the circuitry to the counter electrode) is proportional to the diffusional flux of $H_2O_2$. Accordingly, a raw signal may be produced that is representative of the concentration of analyte in the user's body, and therefore may be utilized to estimate a meaningful analyte value. A CGM sensor can measure analyte levels in, e.g., interstitial fluid.

Figure 3:
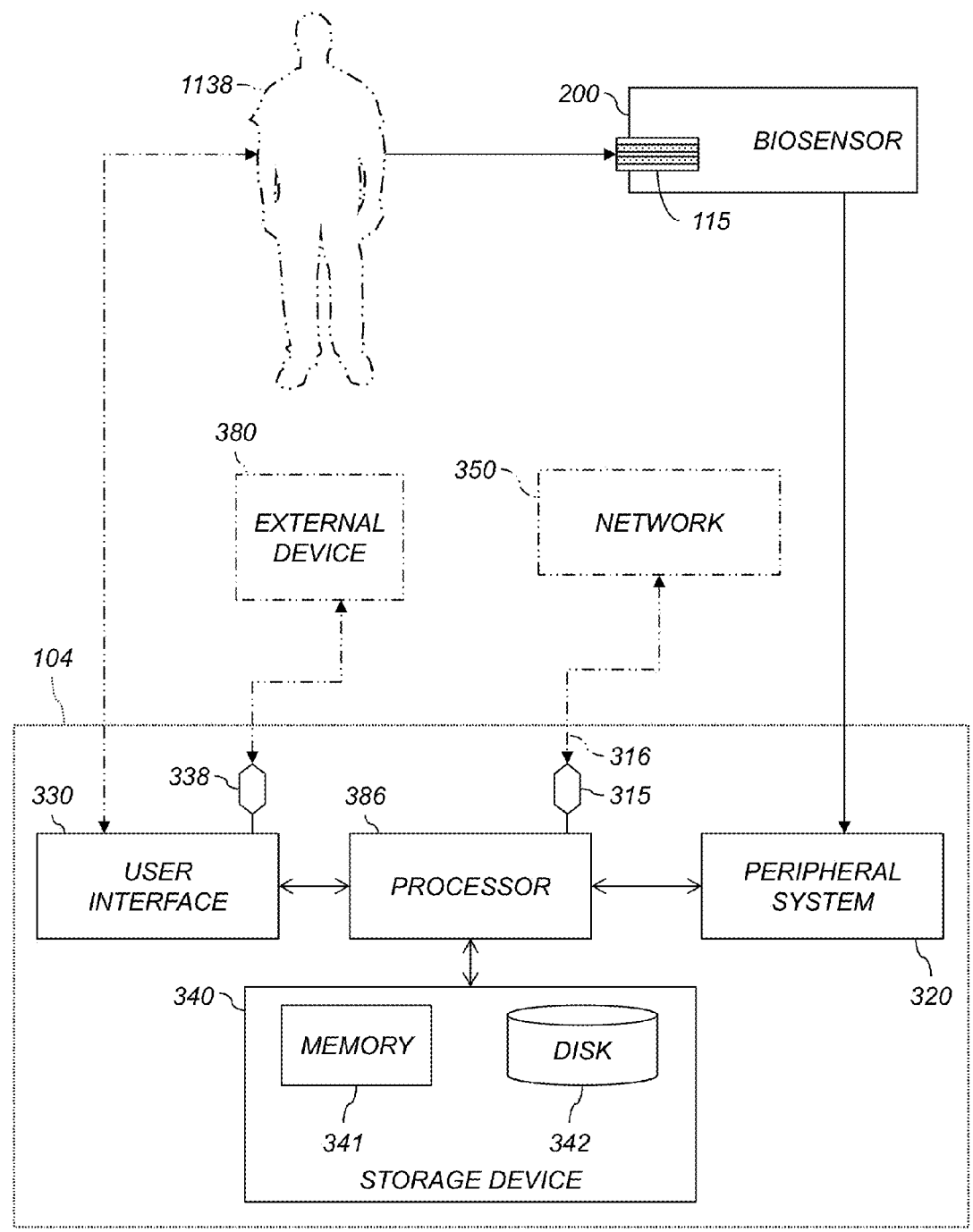
FIG. 3 shows an exemplary system for the management of blood analyte.

FIG. 3 shows an exemplary system for the measurement or management of blood analyte, including data-processing components for analyzing data and performing other analyses and functions described herein, and related components. A subject 1138, a network 350, and an external device 380 are not part of the system but are shown for context. The controller 104 can communicate with the network 350 or the external device 380.

The controller 104 communicates with a biosensor 200, e.g., FIG. 2, that is adapted to receive a fluid sample, e.g., a whole blood sample or control solution sample, and provide analyte data corresponding to a analyte level of the fluid sample. In an example, the biosensor 200 measures respective blood analyte levels of the subject 1138 at certain times or time intervals, e.g., continually or intermittently, and provides respective analyte data indicating each measured analyte level. An example of a biosensor 200 using an episodic analyte meter 114 and a test strip 115 is discussed above with reference to FIG. 2. The biosensor 200 can also include a continuous-glucose-monitoring (CGM) device. The term "continuous" is convenient, but not strictly accurate. In practice, CGM sensors generally sample glucose on a regular time scale, e.g., once per five minutes.

The controller 104 includes a processor 386 that receives the analyte data from the biosensor 200. The controller 104 can also include a peripheral system 320, a user interface 330, and a storage device 340, each communicatively connected to the processor 386. The processor 386 can be communicatively connected to a network 350, e.g., the Internet or an X.25 or other network, as discussed below.

The processor 386 includes one or more data processor(s) that implement processes of various embodiments described herein. A "data processor" is a device for processing data and can include a central processing unit (CPU) or other microprocessor, a microcontroller, a field-programmable gate array (FPGA), a programmable logic device (PLD), a programmable logic array (PLA or PAL), or any other device configured for processing, managing, or handling data as described herein, whether implemented with electrical, magnetic, optical, biological components, or otherwise.

The phrase "communicatively connected" includes any type of connection, wired or wireless, between devices, data processors, or programs in which data can be communicated. Subsystems such as the peripheral system 320, the user interface 330, and the storage device 340 are shown separately from the processor 386 but can be stored completely or partially within the processor 386.

The storage device 340 includes or is communicatively connected with one or more tangible non-transitory computer-readable storage medium(s) configured to store information, including the information needed to execute processes according to various embodiments. A "tangible non-transitory computer-readable storage medium" as used herein refers to any non-transitory device or article of manufacture that participates in storing instructions which may be provided to the processor 386 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Embodiments of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct the processor 386 to perform a particular series of operational steps when loaded, thereby implementing functions or acts specified herein.

In an example, the storage device 340 includes a memory 341, e.g., a random-access memory, and a disk 342, e.g., a tangible computer-readable storage device such as a hard drive or a solid-state flash drive. Computer program instructions are read into the memory 341 from the disk 342, or a wireless, wired, optical fiber, or other connection. The processor 386 then executes one or more sequences of the computer program instructions loaded into the memory 341, as a result performing process steps and other processing described herein. In this way, the processor 386 carries out a computer implemented process that provides for technical effects of converting analyte to signal representative of analyte data and communicating that data. For example, blocks of the flowchart illustrations or block diagrams herein, and combinations of those, can be implemented by computer program instructions. The memory 341 can also store data used by running programs, e.g., point totals as described below.

Program code to carry out methods described herein can execute entirely on a single processor 386 or on multiple communicatively-connected processors 386. For example, code can execute wholly or partly on a user's computer and wholly or partly on a remote computer, e.g., a server. The remote computer can be connected to the user's computer through a network. The user's computer or the remote computer can be non-portable computers, such as conventional desktop personal computers (PCs), or can be portable computers such as tablets, cellular telephones, smartphones, or laptops.

The peripheral system 320 can include one or more devices configured to provide digital content records or other data to the processor 386. In this example, the biosensor 200 is connected to the processor 386 via the peripheral system 320. The biosensor 200 can also be directly connected to the processor 386. The peripheral system 320 can also include digital still cameras, digital video cameras, cellular phones, or other data processors. The peripheral system 320 can also include one or more bus bridge(s), e.g., to operatively connect devices having USB, FIREWIRE, RS-232, or other interfaces to the processor 386. The processor 386, upon receipt of data from a device in the peripheral system 320, can store that data in the storage device 340.

The user interface 330 can include a mouse, a keyboard, another computer (connected, e.g., via a network or a null-modem cable), a microphone and speech processor or other device(s) for receiving voice commands, a camera and image processor or other device(s) for receiving visual commands, e.g., gestures, one or more touch sensor(s), button(s), switch(es), or any other device or combination of devices from which data is input to the processor 386. In this regard, although the peripheral system 320 is shown separately from the user interface 330, the peripheral system 320 can be included as part of the user interface 330. In at least one embodiment, the user interface 330 can be operated by the subject 1138.

The user interface 330 also can include a display device, a processor-accessible memory, or any device or combination of devices to which data is output by the processor 386. In this regard, if the user interface 330 includes a processor-accessible memory, such memory can be part of the storage device 340 even though the user interface 330 and the storage device 340 are shown separately in FIG. 3.

In various embodiments, the user interface 330 includes an external connection terminal 338. The external connection terminal 338 is adapted to selectively convey data between the processor 386 and the external device 380. The external device 380 can be, e.g., a personal computer, computerized kiosk, or medical device used by a doctor or other medical caretaker. The external connection terminal 338 can include components that establish wireless or wired data links. In an example, the external connection terminal 338 includes a USB B jack or other USB device-side jack to which the subject 1138 or anther user can connect a USB cable. This permits establishing communications with, e.g., a personal computer having a USB host. In another example, the external connection terminal 338 includes a BLUETOOTH radio adapted to communicate with one or more other nearby BLUETOOTH device(s).

In various embodiments, a network interface 315 is coupled via a communications link 316 to the network 116. The network interface 315 is configured to selectively convey data bidirectionally between the processor 386 and the network 116 via the communications link 316. For example, the network interface 315 can be an integrated services digital network (ISDN) card or a modem to provide a data communication connection to a corresponding type of telephone line. As another example, the network interface 315 can be a network card to provide a data communication connection to a compatible local-area network (LAN), e.g., an Ethernet LAN, or wide-area network (WAN). Wireless links, e.g., WiFi or GSM, can also be used. The network interface 315 sends and receives electrical, electromagnetic or optical signals that carry digital data streams representing various types of information across the communications link 316 to the network 116 or other networks or network-attached devices. The communications link 316 can be connected to the network 116 via a switch, gateway, hub, router, or other networking device.

The processor 386 can send messages and receive data, including program code, to and from the network 116 via the communications link 316 and the network interface 315. For example, a server in the network 116 can store requested code for an application program (e.g., a JAVA applet or JAVASCRIPT script) on a tangible non-volatile computer-readable storage medium to which the server is connected. The server can retrieve the code from the medium and transmit it to the processor 386 via the Internet, a local ISP, a local network, and the network interface 315. The received code can be executed by the processor 386 as it is received, or stored in the storage device 340 for later execution.

The user interface 330 is adapted to provide a menu of functions to a user and successively receive a plurality of menu choices. Menus, functions, and choices are described below with reference to FIG. 4. The storage device 340 holds data defining a first action criterion. The processor 386 records the received menu choices and compares the menu choices to a first action criterion, so that when the stored menu choices satisfy the first action criterion, the processor 386 automatically adds a first additional function to the menu of functions.

Figure 4:
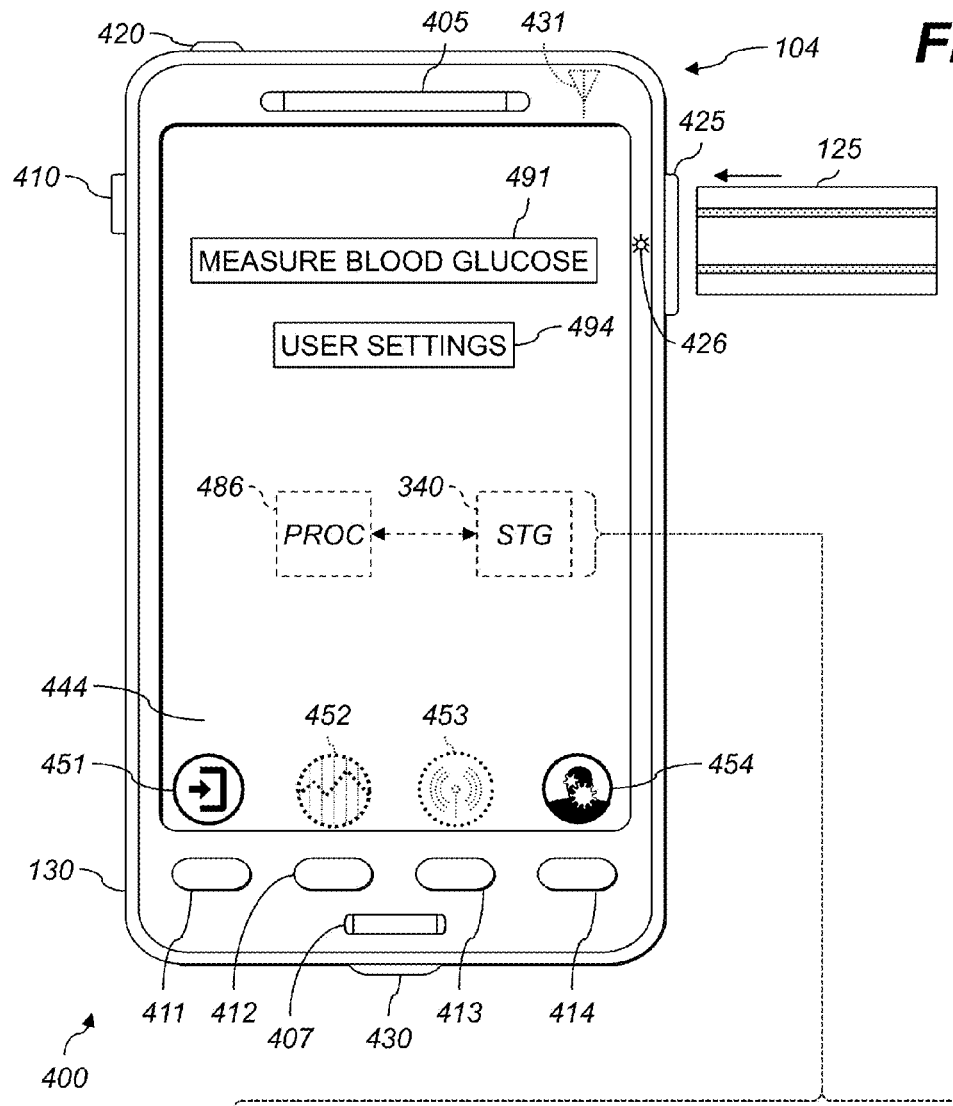
FIG. 4 shows an exemplary analyte measurement system and stored data therein.
Figure 5:
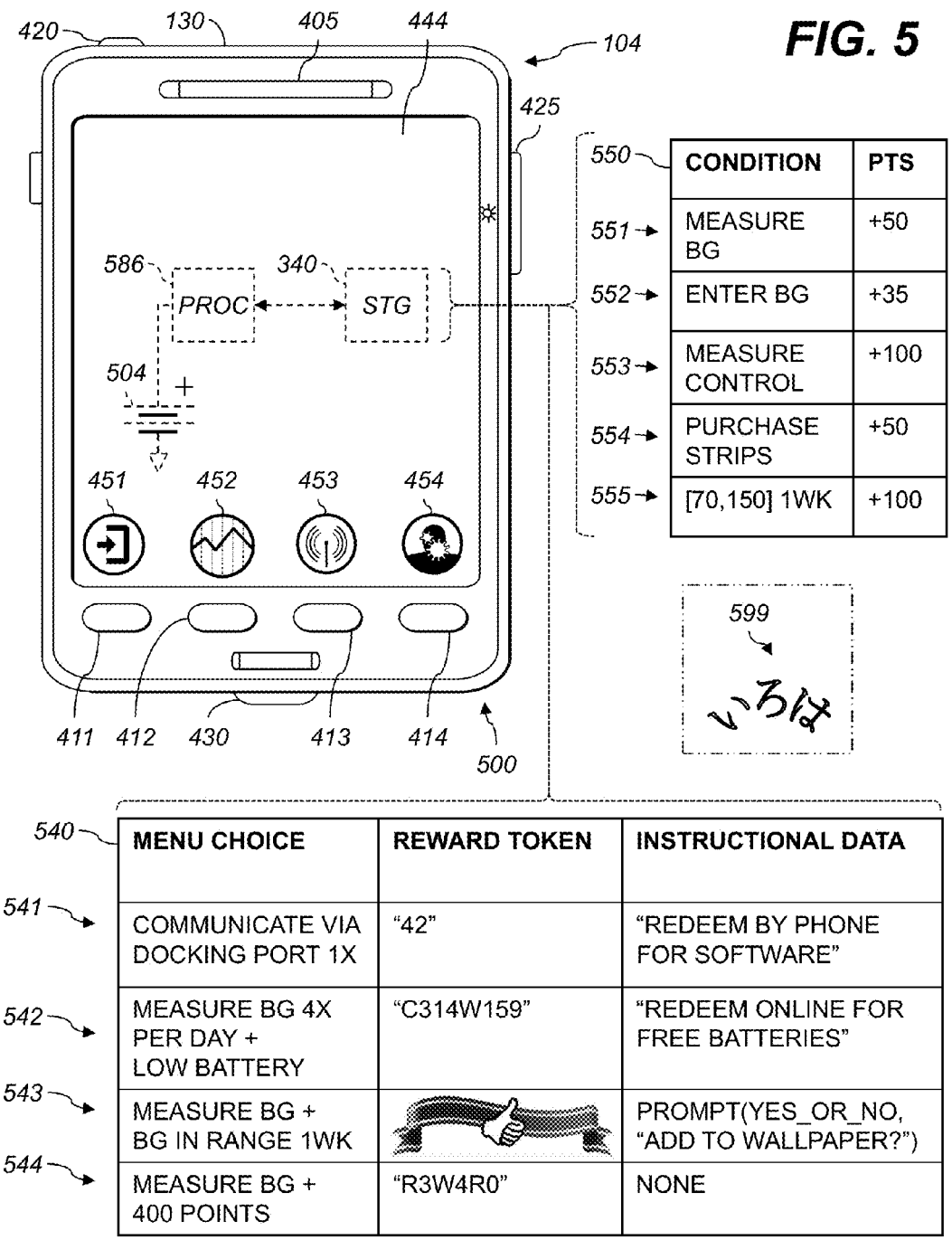
FIG. 5 shows exemplary analyte measurement apparatus and stored data therein.

Throughout this disclosure, e.g., with reference to FIGS. 4 and 5, data stored in the storage device 340 are described. These data include, e.g., action criteria. In various embodiments, these data can be programmed into an analyte measurement device (or system or apparatus) during production or at another time before the user receives the device. In various embodiments, some or all of these data can be programmed into the device by a healthcare provider, e.g., using the external device 380. Some of the data can be fixed at production and other data modifiable by a healthcare provider.

FIG. 4 is a schematic diagram showing an example of an analyte measurement system 400 and stored data therein. FIG. 4 illustrates menus, functions, action criteria, and additional functions. The exemplary system 400 of FIG. 4, which can include a smartphone, includes a controller 104 having a housing 130 and a display 444. A joystick pointing device (not shown) can be used. A touchscreen can also be used instead of the display 444. Disposed within the housing 130 are the processor 486 (e.g., the processor 386, FIG. 3), the storage device 340, and an antenna 431. Disposed on the housing 130 are a switch 410, soft keys 411, 412, 413, 414, a headphone jack 420, a docking port 430, an earpiece 405, and a mouthpiece 407. Disposed in or on the housing 130 is a strip port connector 425 adapted to receive the test strip 115. An example of a strip port connector 425 disposed in the housing is found in the glucose meter of the ONE-TOUCH PING system referenced above. The user can insert the test strip 115 through an opening in the housing 130 into the strip port connector 425. In another example, a shrouded connector such as the SWITCHTECH SW-BGM four-pin, 1.25 mm-pitch dual-direction withdrawal connector can be mounted on the housing 130 to receive the test strip 115.

The system 400 receives user inputs requesting various functions and performs those functions (e.g., measures blood glucose). The user interface 330 of the system 400, including its form factor, actuatable control buttons (if any), a display (if any), or other input or output devices, informs the user what functions are available at any given time. As used herein, a "menu" includes this information about the available functions. The user interface 330, FIG. 3, of the analyte measurement system 400 provides the menu of functions to the user. The user interface 330 receives a menu choice when the user provides input to the system 400 to select one of the functions referenced in the menu. The system 400 can provide different menus at different times, depending on the available functions at that time.

The menu can include various options presented on the display 444 and selected with a pointing device, e.g., conventional drop-down menus or graphical buttons selectable with a mouse or joystick. The menu can also include choices made available by off-screen devices, e.g., switch 410, or combinations of off-screen devices and visible indications on a display, e.g., the soft keys 411, 412, 413, 414. A menu can include choices presented in different locations, e.g., in two different areas on the display 444.

In an example, if the user clicks on (with a pointing device) or otherwise selects (e.g., by touching on a touchscreen 144) the graphical button 491 ("MEASURE BLOOD ANALYTE"), or pushes the soft key 411 labeled by the soft-key label 451, the controller 104 will take a blood analyte measurement. If the user clicks on or otherwise selects the graphical button 494 ("USER SETTINGS"), or pushes the soft key 414 labeled by the soft-key label 454, the controller 104 will display a dialog box or other screen soliciting input from the user, e.g., username, gender, diabetes type, or insulin sensitivity factor (ISF). The graphical buttons 491, 494 and the soft keys 411, 414 with the respective soft-key labels 451, 454 present portions of the menu. As the user interacts with the system 400 over time, the user interface 330 successively receives a plurality of menu choices. For example, a user can first press the graphical button 494 or the soft key 414 to enter settings, then subsequently insert the test strip 125 or press the graphical button 491 or the soft key 411 in order to take a blood analyte measurement.

As discussed above, the menu is presented by the user interface 330 and informs the user about available functions of the system 400. Embedded systems, such as a analyte meter 114 or a controller 104, often indicate available functions to the user via components of the system that the user can physically manipulate to request those functions be carried out. In an example, the "+" and "−" buttons on a television remote control are increase-volume and decrease-volume buttons, respectively. The existence and markings of these buttons informs the user that the functions of increasing volume and decreasing volume are available. Therefore, included in the menu of functions provided to the user by the user interface of the remote control are the functions of increasing volume and decreasing volume. When the user presses the "+" or "−" button, the user interface receives a menu choice of the increase-volume or the decrease-volume function, respectively. In general, a menu can include information about functions of a device even when that information is presented by physical components rather than wholly or partly via a display screen.

Referring specifically to the analyte measurement system 400, the existence of the docking port 430 indicates that connecting the controller 104 to an external device 380, FIG. 3, via the docking port 430 is an input to which the system 400 is prepared to respond. Therefore, the menu presented by the system 400 having the docking port 430 includes the function of connecting to an external device 380, FIG. 3. When the user connects a cable or other link to the docking port 430, the user is choosing "communicate with external device" from the menu and the user interface 330 receives that menu choice.

In another example, the strip port connector 425 is part of the user interface 330, and the existence or markings of the strip port connector 425 indicate the system 400 can perform a function upon receiving the test strip 125. Therefore, the menu presented by the user interface 330 includes the function of receiving a test strip for processing. When the user inserts the test strip 125 into the strip port connector 425, the user is providing an input to the system, namely, choosing "process inserted test strip" from the menu. In response, the system 400 performs a blood-analyte reading using the inserted test strip 125. Other components of the user interface 330 can be used to indicate whether certain functions are available. For example, the light-emitting diode (LED) 426 can be illuminated when the controller 104 is prepared to initiate a blood-analyte test in response to insertion of the test strip 125 in the strip port connector 425. In this example, the function of receiving a test strip 125 is included in the menu presented by the user interface 330 only when the light-emitting diode (LED) 426 is illuminated.

In another example, for a user to connect the controller 104 to a network 350, FIG. 3, e.g., via USB or BLUETOOTH, is to make a menu choice to direct the controller 104 to communicate with the network 350. The user can also provide menu choices by, e.g., pushing the soft keys 411, 414, toggling the switch 410, or connecting to the headphone jack 420.

The storage device 340 holds data defining a first action criterion. An example is shown in the inset 440. A data record 441 includes the first action criterion, in this example a menu choice. The data record 441 also holds a corresponding additional function, and optionally other data. The processor 486 records the received menu choices (e.g., in the storage device 340) and compares the received menu choices to the first action criterion. When the stored menu choices satisfy the first action criterion, the processor 486 automatically adds a first additional function to the menu of functions. Note that, in this example, the soft-key labels 452 and 453 are initially not visible, so their corresponding functions are not included on the menu.

In this example, the inset 440 shows that the first action criterion in the data record 441 specifies the menu choice "communicate via docking port." That is, when the user connects the external device 380 to the docking port 430, the user is selecting from the menu a choice of communicating with the external device 380 via the docking port 430. The processor 486 compares that menu choice to the first action criterion in the data record 441 and determines that the two match, i.e., the stored menu choice of communicating via the docking port 430 satisfies the first action criterion in the data record 441. The processor 486 therefore automatically adds a first additional function, "make wireless connection," to the menu of functions. In this example, the processor 486 displays the soft-key label 453 above the soft key 413. The menu now indicates that the user can press the soft key 413 to initiate a wireless connection via the antenna 431.

Specifically, in various embodiments, the user interface 330, FIG. 3, includes an external connection terminal 338, FIG. 3 (wireless or wired). One of the functions in the menu is establishing a data connection via the external connection terminal 338. The data that define the first action criterion include a requirement that the data connection be established. In some of these embodiments, the external connection terminal 338 includes a mechanical cable connector (e.g., the docking port 430). The user interface 330 further includes a wireless external connection terminal, e.g., the antenna 431. The first function is wireless communications via the wireless external connection terminal.

The data stored in the storage device 340 can further define a second action criterion or any number of additional action criteria. In this example, a data record 442 holds the second action criterion. The processor 486 is configured to compare the menu choices to the second action criterion in the data record 442, so that when the stored menu choices satisfy the second action criterion, the processor 486 automatically adds a second additional function to the menu of functions. In the example shown, the second action criterion in the data record 442 is "measuring blood analyte (BG) four times per day." The corresponding additional function is "graphing blood analyte results." The processor 486 stores multiple received menu choices, e.g., with a timestamp for each. (As used herein, the term "timestamp" refers to a record of date, time, or both date and time, e.g., a UNIX count of seconds since Jan. 1, 1970.) The processor 486 is programmed to determine how many times the blood-analyte-measurement menu choice has been received on any given day. If that number exceeds four times in one day, the second action criterion is satisfied. The processor 486 then adds the second additional function to the menu, e.g., by displaying the soft-key label 452 on the display 444. In various embodiments, the data that define the second action criterion include a requirement that the first action criterion be satisfied. Criteria can be made dependent on each other in any desired combination. Other examples of action criteria are discussed below with reference to FIG. 5.

The data record 442 shows an example of an action criterion using data in addition to the stored menu choice, specifically, timestamps of the stored menu choices. In various embodiments, the analyte data are also used. Specifically, in these embodiments the processor 486 is further configured to successively record a plurality of values of the analyte data and to analyze the recorded analyte values. The data that define the first action criterion can include, e.g., a requirement that the recorded analyte values be within a selected range during a selected time period.

The data record 443 shows an example of such a requirement. A third action criterion, stored in the data record 443, is that blood analyte be maintained within the range [70,150] mg/dL for n weeks, with at least k BG readings being taken per day. The other data in the data record 443 specify that n=1 and k=4. The k requirement implies that the menu choice to take blood analyte readings, or a menu choice to enter blood analyte readings from another device, must be chosen from the menu at least k times per day in order to satisfy the third action criterion. In addition to storing menu choices and determining whether they meet the k criterion, the processor 486 is configured to inspect the recorded analyte values resulting from record-BG or enter-BG functions to determine whether the recorded analyte values meet the n criterion. Once the third action criterion is satisfied, suggesting the user is carefully controlling BG, the function of customizing the meter's alert limits, e.g., within ranges set by a health-care provider, is added to the menu (e.g., as part of the user settings dialog invoked by the graphical button 494). Other examples of BG-related action criteria are discussed below with reference to the data record 543 shown in FIG. 5.

In another example, the data that define the third action criterion (or another one of the stored action criteria) further include a requirement that the recorded analyte values be within a second selected range during a second selected time period, the second selected range being a proper subset of the selected range and the second selected time period following after the selected time period. For example, the action criterion can specify that BG should be maintained in [60,160] for the first week of a given month and within [70,150] for the second week of a given month. The processor is configured to analyze the recorded analyte values to determine whether the given ranges have been satisfied. The action criterion can also specify that BG should be within a given range a certain percentage of a given time period, e.g., within [70,150] for 95% of a given month.

In another example, the data that define the first action criterion include a requirement that a selected one of the menu choices be received at least a selected number of times during a selected time period. Such action criteria can be, e.g., n times total per week, or an average of m times per day. In various embodiments, the first function can include meal tagging, pattern messaging, wireless communication (e.g., for high-frequency testers), storage and display of a plurality of values of the analyte data, or time averaging over a selected time period shorter than 30 days. In various embodiments, the data that define the first criterion can include a requirement of transmitting one or more values of the analyte data via an external connection terminal of the analyte measurement system; more than a selected number of times per day, receiving a menu choice to test blood analyte using the biosensor; or more frequently than a selected frequency (e.g., more than once every six hours), receiving a menu choice to test blood analyte using the biosensor. Any action criterion can include any combination of menu choices or other action criteria described herein.

New users of an analyte-measurement system may not be aware of the full range of possible functions. Moreover, restricting the number of functions menu advantageously reduces the probability of user confusion. In various embodiments, the processor is further configured to, after adding the first additional function to the menu of functions, present a notification corresponding to the first additional function via the user interface. The notification can include, e.g., a training message or other content to help the user learn to use the newly-available function.

A technical effect of adding additional functions in response to action criteria is to provide each user access to functions that user is more likely to need. This advantageously keeps the user interface of an analyte measurement system simple, while providing functions from which users can benefit.

FIG. 5 shows an analyte measurement apparatus according to various embodiments, and data stored therein. The exemplary apparatus 500 of FIG. 4, which can include a smartphone, includes a controller 104 having a housing 130 and a display 444. The housing 130 holds the user interface 330 (e.g., the display 444), a storage device 340, a processor 586, and a biosensor 200.

The biosensor 200, FIG. 2, includes a strip port connector 425, corresponding electronics (not shown), and a test strip (not shown; the test strip 125 is shown in FIG. 4). The biosensor 200 is adapted to receive a fluid sample and provide analyte data corresponding to an analyte level of the fluid sample. The apparatus 500 also includes a user interface 330, FIG. 3, adapted to provide a menu of functions to a user and successively receive a plurality of menu choices. Menus, functions, and choices are as discussed above with reference to FIG. 4. In various aspects, the user interface 330 includes a soft-copy display 444, e.g., an organic light-emitting diode (OLED) display or liquid-crystal display (LCD), or an audio output, e.g., a headphone jack 420, an earpiece 405, or a speaker (not shown). Also shown are exemplary soft-key labels 451, 452, 453, 454 corresponding to the soft keys 411, 412, 413, 414 respectively.

The storage device 340 holds data defining a first action criterion. Action criteria are as discussed above with reference to FIG. 4. The processor 586 (e.g., the processor 386, FIG. 3) is operatively connected to the user interface 330, the biosensor 200, and the storage device 340 to record the received menu choices and compare the menu choices to the first action criterion. When the stored menu choices satisfy the first action criterion, the processor 586 automatically presents a reward token via the user interface 330. The reward token can include a code or other information redeemable outside the meter for a reward or recognition. The reward token can also include information or content used in the analyte measurement apparatus 500, excluding additional functions (which are discussed above with reference to FIG. 4). The reward token can be presented, e.g., via the display 444 or via a speech synthesizer driving the earpiece 405 or the headphone jack 420.

In various embodiments, the processor 586 is configured to present a unique redemption code as the reward token. The redemption code can include one or more letters, numbers, accents, punctuation marks, ideographic or syllabic signs, whitespace characters, or combinations thereof. The redemption code can be presented in a particular language and can include a sequence of characters or signs a person that knows that language is able to reproduce, such as an alphabetic string in English ("ABC") or a sequence of hiragana characters in Japanese (see the exemplary unique redemption code 599, FIG. 5: iroha). In some examples, the storage device 340 further holds a unique identifier, e.g., a serial number of the apparatus 500. The processor 586 is configured to determine the unique redemption code using the stored unique identifier. For example, the unique redemption code can begin or end with, or otherwise include, part or all of the unique identifier. The unique redemption code can also include a cryptographic hash of a secret with the serial number of the apparatus.

In some exemplary embodiments, the user interface includes a soft-copy display or an audio output, and does not include a hard-copy output such as a printer. The processor 586 is configured to present the unique redemption code by displaying a visual representation of the unique redemption code on the soft-copy display or by playing an audio representation of the unique redemption code via the audio output.

The inset 540 shows examples of action criteria and other data stored in the storage device 340. The data record 541 shows that the action criterion is communicating via the docking port for the first time ("1×"). The reward token is the unique redemption code "42". When the user uses the docking port 430 to communicate for the first time, the processor 586 will provide the redemption code to the user. Each action criterion can include data indicating the processor should provide the reward token only the first time that action criterion is satisfied, or the nth time, or any combination, or each time the criterion is satisfied without limit. Other examples of action criteria are discussed above with reference to FIG. 4.

In various aspects, the storage device 340 further holds instructional data corresponding to the first reward token. The processor 386 is further configured to present the stored instructional data with the reward token via the user interface. The reward token and the instructional data do not have to be presented simultaneously. For example, the reward data can be presented before or after the reward token or in response to a menu choice received while the reward token is being presented. In the exemplary data record 541, the instructional data include an explanatory message indicating that the unique redemption code is redeemable by a user for additional software for the external device 380, and that the redemption can be performed by calling a telephone number, e.g., a telephone number specified in the instructional data or stamped into or marked on the housing 130. This advantageously provides additional software functions to users that are likely to benefit from those functions, but without burdening users who do not connect the apparatus to an external device 380 via the docking port 430.

In another example, a data record 542 includes a second action criterion. The processor 586 monitors the state of a battery 504 in the controller 104. When the battery 504 reaches a low-battery threshold, the processor 586 analyzes the stored menu choices and respective timestamps to determine if the user is choosing to measure or enter BG data at least four times per day. If so, the second action criterion is satisfied. The reward token from the data record 542 is provided to the user, optionally with the instructional data from the data record 542, e.g., "redeem online for free batteries." This is an explanatory message indicative that the code is redeemable for a replacement battery. This reward advantageously provides users that frequently test their blood-analyte levels an incentive to continue doing so, even when the batteries in the controller 104 run low.

An exemplary data record 543 includes data defining a third action criterion. These data specify that a menu choice to measure or enter BG data be received at least once. The processor 586 is also configured to inspect the recorded analyte values resulting from record-BG or enter-BG functions to determine whether the recorded analyte values have been in a selected range for one week, e.g., as discussed above with reference to the data record 443, FIG. 4. The reward token in this instance is not a unique redemption code, but instead an image celebrating the maintenance of the user's blood analyte within range. The image can be, e.g., stored in the storage device 340 in an image format or stored or transmitted as a "data" URI or in another encoded form. In this example, the instructional data in the data record 543 include a script. The processor 586 interprets the instructional data. In response to the PROMPT( ) function in the script, the processor 586 shows the image and the text "Add to wallpaper?" and provides the user a "Yes" input and a "No" input. If the user selects "Yes," the image is added to a wallpaper image displayed as a background on the display 444.

In other examples, explanatory messages included in the instructional data can include a message indicative that the code is redeemable for a pharmaceutical or first-aid item or a message indicative that the code is redeemable for a discount at a retailer (whether brick-and-mortar or online). The message can also be indicative that the code is redeemable for graphical or auditory content to be presented via the user interface. Examples of such content include new skins, themes, splash screens, wallpaper images, and alert sounds (e.g., ringtones).

An exemplary data record 544 in the storage device 340 shows a fourth action criterion using a point system. The storage device 340 holds a plurality of point increments corresponding to a plurality of the functions. Exemplary functions and point increments are shown by the inset 550. In the data records 551, 552, 553, and 554, the "condition" is that the listed function is performed. The processor 586 is configured to add to a stored point total the stored point increment for the respective function(s) corresponding to each of the received menu choices. The point increment can be negative or positive, and can be integer- or real-valued. The stored point total can be initialized to zero or to some nonzero initial point value before the user receives or activates the apparatus 500. The processor 586 can be configured to add the point increment only if the function has not been performed within a selected time period.

In the example shown, each time the processor 586 receives from the user a menu choice to measure blood analyte using the biosensor, the processor 586 adds 50 points to the stored point total, as indicated in the data record 551. Entering BG data measured by another device earns (i.e., causes the processor 586 to increment the stored point total by) 35 points (data record 552). Performing a control-solution test using the biosensor earns 100 points (data record 553). The data record 553 can also include a condition that control-solution measurement not have been performed within the last week in order to earn the point increment. In this way, a user can perform control-solution measurements at any time, but is not permitted to artificially inflate the point total by performing numerous control-solution tests in quick succession. In another example, points can be earned by choosing from the menu a function of transmitting one or more values of the analyte data via the external connection terminal 338 of the analyte measurement system.

The data record 554 shows that purchasing test strips earns 50 points. Test strips can be purchased via a menu choice (e.g., over a communications link 316). Alternatively or additionally, a menu choice can be provided permitting the user to enter a unique code printed on a package of test strips or other biosensors, and the processor can verify the entered code against known rules for valid codes (e.g., checksums or secure hashes with a hard-coded secret) and add the 50 points to the stored point total only if verification succeeds.

Referring back to the inset 540, in the data record 544, the data that define the fourth action criterion include a requirement that the stored point value reach a selected point threshold, e.g., 400 points. When the stored point value reaches 400 points and the user has measured BG at least once, the fourth action criterion is satisfied and the reward token is presented. In at least some embodiments, the processor is configured to present the reward token by providing a unique redemption code and deducting the selected point threshold (e.g., 400 points in the data record 544) from the stored point total. This advantageously permits the user to accumulate points and redeem the accumulated points for reward tokens.

Point increments can also be assigned to combinations of functions, e.g., performing a control-solution test followed by performing a blood-analyte test. Combinations can be limited in various ways. For example, points can be added to the stored point total when two specified functions are invoked within a certain period of time.

Point increments can also correspond to conditions other than the performance of functions or the receipt of menu choices. In at least one embodiment, point increments can be earned for keeping BG within a certain range. In the exemplary data record 555, the storage device 340 stores a target blood-analyte range ([70,150]), a target time period (one week), and a corresponding target point increment (+100 points). The processor 586 is configured to successively record a plurality of values of the analyte data and to analyze the stored values. The processor 586 adds the target point increment to the stored point total when the stored values are within the target range during the target time period. This target point increment can be earned without regard to which functions are performed during the target time period, since the "condition" field of the data record 555 does not include a requirement to perform any function.

In various embodiments, the processor 586 is further configured to determine a future portion of the target time period and provide an indication to the user of the determined future portion and the target point increment. Continuing the example of the data record 555, after five days of the seven-day target time period have passed, if the processor 586 determines that BG has been within the target blood-analyte range for those five days, the processor 586 can present an encouragement message to the user via the user interface 330. An exemplary message is "If you stay in range for another 2 days you will earn 100 points!". The processor 586 can be configured to check BG values one or more times per day or week, and can be configured to perform those checks starting at the beginning of the target time period, starting three days before the end of the target time period, starting half-way through the target time period, or at other start times. Providing encouragement messages can advantageously provide the user incentive to continue performing behaviors that may have a positive effect on the user's health.

Just as users may not be aware of the full range of available functions, users may not be aware of the range of point-earning actions, or may have forgotten that certain actions earn points. In various embodiments, the processor 586 is further configured to use the stored menu choices to determine a function that does not correspond to a menu choice received within a selected time period, e.g., one year or one month. The processor 586 can store timestamps with the received menu choices, or can store a single timestamp for each function indicating the most recent time a menu choice corresponding to that function was received. The processor 586 is configured to provide an indication via the user interface 330 of the determined function and the corresponding stored point increment. In an example, on Mar. 14, 2015, the processor 586 can determine that a control solution test was last performed on Aug. 3, 2014. The processor 586 can then present a message that "it has been 223 days since you last performed a control solution test—if you perform one, you will earn 100 points!". This can advantageously inform the user about available functions or point-earning conditions, and encourage corresponding user behaviours.

Figure 6:
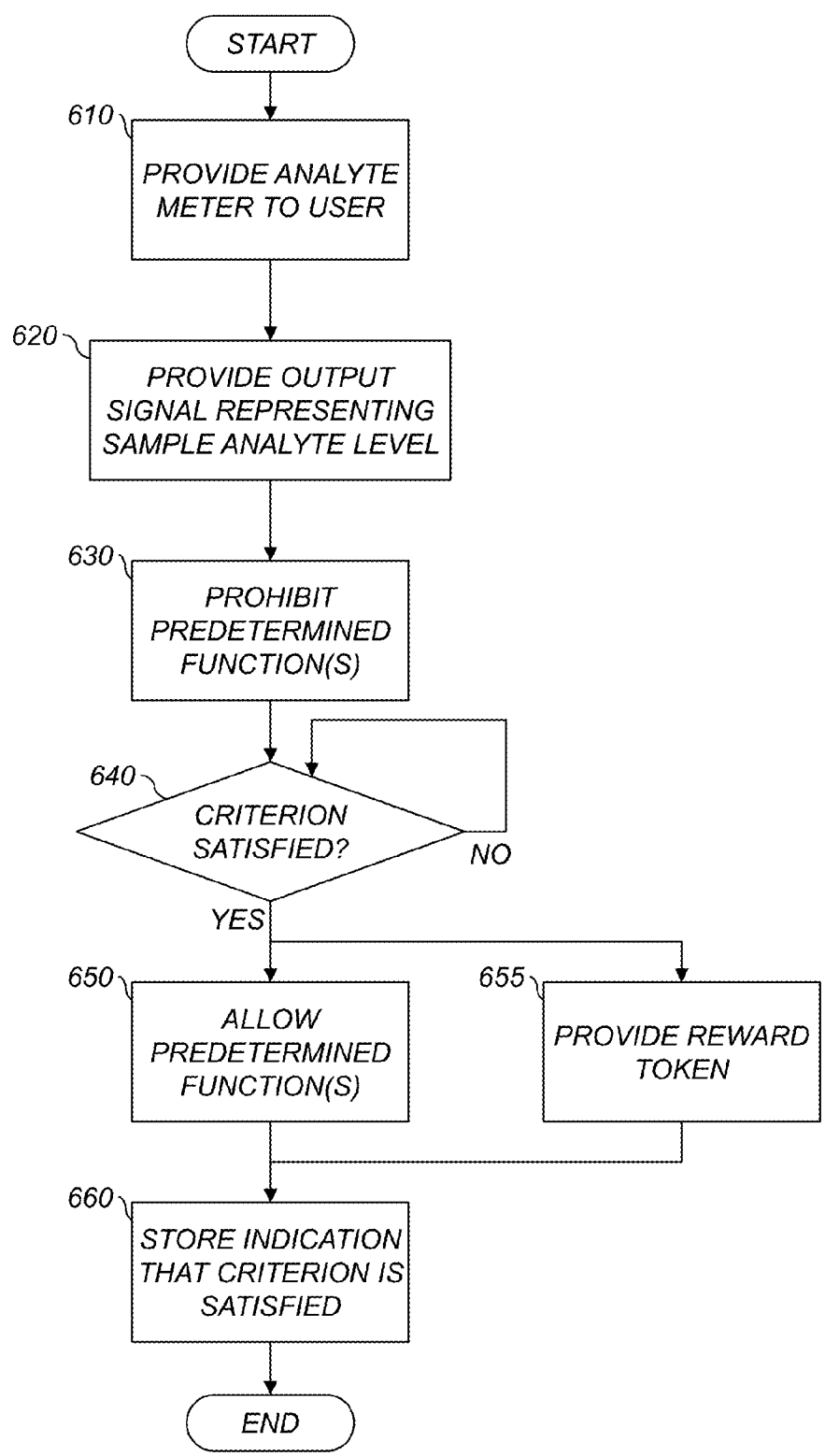
FIG. 6 is a flowchart illustrating exemplary methods for operating an analyte meter.

FIG. 6 is a flowchart illustrating exemplary methods for operating an analyte meter. As provided for above, a method of operating an analyte meter is provided in which the user is prevented from obtaining certain features of the meter until certain actions have been completed on the meter and the user is rewarded with additional features of the meter. In particular, the method includes providing an analyte meter to the user in step 610, applying a fluid sample to a biosensor so that an analyte in the fluid sample is transformed into an enzymatic product by a signal provided with a processor of the meter to provide an output signal representative of the level of the analyte in the sample in step 620, prohibiting at least one predetermined function of the analyte meter in step 630 until a first action criterion is satisfied (tested in decision step 640), and allowing at least one predetermined function in step 650 when the first action criterion is satisfied. In step 660, data indicating that the first action criterion is satisfied can be stored in a storage device, e.g., the storage device 340, FIG. 3, so that the at least one predetermined function will continue to be available. The at least one predetermined function may include issuance of a reward token. Alternatively, the at least one predetermined function may include at least one of a blood analyte test performed with the biosensor, a control-solution test performed with the biosensor, a unique identifier of a package of biosensors entered in the processor, one or more values of the analyte data transmitted via an external connection terminal of the analyte measurement system, or combinations thereof. Alternatively or additionally, when the first action criterion is satisfied, a reward token can be provided as discussed above (step 655). In some embodiments, steps 630, 650 are not performed and step 655 is performed.

In view of the foregoing, embodiments of the invention advantageously provide users with improved usability of their blood-analyte measurement devices or incentives to use such devices. A technical effect of biosensors and processing described herein is to convert analyte levels in a blood sample to data. A technical effect of providing reward tokens to users is to permit user activities performed using a analyte measurement apparatus to result in benefits outside the analyte measurement apparatus. Various embodiments permit healthcare providers to determine which menu choices will be rewarded with reward tokens or will earn points, advantageously permitting those healthcare providers to create incentive structures customized for particular patients. Various embodiments both add additional functions and present reward tokens, according to the data stored in the storage device 340. This further permits healthcare providers to design appropriate incentives for each particular patient.

PARTS LIST FOR FIGS. 1-6

100 system
102 drug delivery device
104 controller
106 infusion set
108 flexible tubing
112 radio frequency communication link
114 analyte meter
115 test strip
116 network
118 wireless communication network
125 test strip
126 server
128 storage device
130 housing
144 touchscreen
200 biosensor
201, 202 electrical contact pads
204 planar substrate
210, 220 electrodes
230 sample-receiving chamber
315 network interface
316 communications link
320 peripheral system
330 user interface
338 external connection terminal
340 storage device
341 memory
342 disk
350 network
380 external device
386 processor
400 system
405 earpiece
407 mouthpiece
410 switch
411, 412, 413, 414 soft keys
420 headphone jack
425 strip port connector
426 light-emitting diode
430 docking port
431 antenna
440 inset
441, 442, 443 data records
444 display
451, 452, 453, 454 soft-key labels
486 processor
491, 494 graphical buttons
500 apparatus
504 battery
540 inset
541, 542, 543, 544 data records
550 inset
551, 552, 553, 554, 555 data records
586 processor
599 unique redemption code
610, 620, 630 steps
640 decision step
650, 655, 660 steps
1138 subject While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. To the extent there are variations of the invention that are within the spirit of the disclosure or are equivalent to the inventions found in the claims, it is the intent that this patent will cover those variations as well.

What is claimed is:

1. An analyte measurement system comprising:
   a) a biosensor that receives a fluid sample and provides analyte data corresponding to an analyte level of the fluid sample, and;
   b) a test meter that receives the biosensor, the test meter comprising:
      i) a user interface that provides a menu of functions to a user and successively receives a plurality of menu choices, the menu of functions initially comprising a limited menu of one or more analyte measurement functions and the user interface including a plurality of labels on a display screen of the test meter corresponding to off-screen switches or soft keys of the user interface, wherein at least one label for a soft key is not visible to the user to provide for at least one unlabeled soft key;
      ii) a storage device holding data defining a first action criterion, the first action criterion based on the state of the test meter or the analyte data, wherein the state of the test meter relates to at least one of the connectivity and functionality of the test meter; and
      iii) a processor operatively connected to the user interface, the biosensor, and the storage device wherein the processor automatically records the received menu choices and the analyte data, and compares the menu choices and the analyte data to the first action criterion, so that when the stored menu choices and the analyte data satisfy the first action criterion, the processor automatically adds a first additional function to the menu of functions and displays a graphical label for the first additional function to the previously unlabeled soft key, the first additional function being a first additional analyte measurement function and comprising one of an analyte measurement graphing function or an analyte measurement alerting function, wherein each of the remaining plurality of labels on the display screen remain unchanged in terms of their prior correspondence to the corresponding off-screen switches or soft keys when the first action criterion is satisfied and the graphical label is displayed for the first additional function to the previously unlabeled softkey.

2. The system according to claim 1, the analyte data further defining a second action criterion, the data that define the second action criterion including a requirement that the first action criterion be satisfied, the processor further configured to compare the menu choices to the second action criterion, so that when the stored menu choices satisfy the second action criterion, the processor automatically adds a second additional function to the menu of functions.

3. The system according to claim 1, the processor further configured to successively record a plurality of values of the analyte data and to analyze the recorded analyte values, the data that define the first action criterion including a requirement that the recorded analyte values be within a selected range during a selected time period.

4. The system according to claim 3, the data that define the first action criterion further including a requirement that the recorded analyte values be within a second selected range during a second selected time period, the second selected range being a proper subset of the selected range and the second selected time period following after the selected time period.

5. The system according to claim 1, the data that define the first action criterion including a requirement that a selected one of the menu choices be received at least a selected number of times during a selected time period.

6. The system according to claim 1, the user interface including an external connection terminal, one of the functions in the menu being establishing a data connection via the external connection terminal, and the data that define the first action criterion including a requirement that the data connection be established.

7. The system according to claim 6, the external connection terminal including a mechanical cable connector, the user interface further including a wireless external connection terminal, and the first function being wireless communications via the wireless external communication terminal.

8. The system according to claim 1, the first additional function being selected from the group consisting of meal tagging, pattern messaging, wireless communication, storage and display of a plurality of values of the analyte data, and time averaging over a selected time period shorter than 30 days.

9. The system according to claim 1, the data that define the first action criterion including a requirement selected from the group consisting essentially of:
   a) transmitting one or more values of the analyte data via an external connection terminal of the analyte measurement system;
   b) more than a selected number of times per day, receiving a menu choice to test blood analyte using the biosensor; and
   c) more frequently than a selected frequency, receiving a menu choice to test blood analyte using the biosensor; and
   d) combinations thereof.

10. The system according to claim 1, the processor further configured to, after adding the first additional function to the menu of functions, present a modification corresponding to the first additional function via the user interface.

* * * * *